(12) United States Patent
Matsuura et al.

(10) Patent No.: US 7,560,284 B2
(45) Date of Patent: Jul. 14, 2009

(54) FINE PARTICLES CONTAINING RARE EARTH ELEMENT AND FLUORESCENT PROBE USING THE SAME

(75) Inventors: Daisuke Matsuura, Shinjuku-ku (JP); Hideshi Hattori, Shinjuku-ku (JP)

(73) Assignee: Dai Nippon Printing Co., Ltd., Tokyo-to (JP)

( * ) Notice: Subject to any disclaimer, the term of this patent is extended or adjusted under 35 U.S.C. 154(b) by 739 days.

(21) Appl. No.: 10/494,782

(22) PCT Filed: Mar. 4, 2003

(86) PCT No.: PCT/JP03/02480

§ 371 (c)(1), (2), (4) Date: May 6, 2004

(87) PCT Pub. No.: WO03/074630

PCT Pub. Date: Sep. 12, 2003

(65) Prior Publication Data

US 2005/0014283 A1 Jan. 20, 2005

(30) Foreign Application Priority Data

| Mar. 5, 2002 | (JP) | 2002-058359 |
| Jul. 26, 2002 | (JP) | 2002-218933 |
| Nov. 15, 2002 | (JP) | 2002-332852 |

(51) Int. Cl.
G01N 33/20 (2006.01)
G01N 33/551 (2006.01)
G01N 21/76 (2006.01)

(52) U.S. Cl. ............ 436/82; 436/73; 436/124; 436/127; 436/133; 436/164; 436/166; 436/172; 436/518; 436/524; 435/7.1; 252/301.4 R; 252/301.4 H (58) Field of Classification Search ............ 436/73, 436/82, 86, 124, 127, 133, 154, 166, 172, 436/518, 528, 524; 435/4, 6, 7.1; 252/301.4 R, 252/301.4 H
See application file for complete search history.

(56) References Cited

U.S. PATENT DOCUMENTS

| 5,674,698 A * | 10/1997 | Zarling et al. ............ 435/7.92 |
| 5,698,397 A * | 12/1997 | Zarling et al. ............ 435/6 |
| 5,736,410 A * | 4/1998 | Zarling et al. ............ 436/172 |
| 5,891,656 A * | 4/1999 | Zarling et al. ............ 435/7.92 |
| 6,132,642 A * | 10/2000 | Kane ............ 252/301.4 S |
| 6,159,686 A * | 12/2000 | Kardos et al. ............ 435/6 |
| 6,299,797 B1 * | 10/2001 | Igarashi et al. ............ 252/301.4 R |
| 6,312,914 B1 * | 11/2001 | Kardos et al. ............ 435/6 |
| 6,399,397 B1 | 6/2002 | Zarling et al. |
| 6,537,829 B1 * | 3/2003 | Zarling et al. ............ 436/514 |
| 6,699,406 B2 * | 3/2004 | Riman et al. ............ 252/301.36 |
| 7,008,559 B2 * | 3/2006 | Chen ............ 252/301.6 S |
| 2006/0140240 A1 * | 6/2006 | Chen ............ 372/69 |

FOREIGN PATENT DOCUMENTS

| EP | 0842898 | 11/1997 |
| EP | 1052278 | 5/2000 |
| JP | 48-026685 | 4/1973 |
| JP | 03-141115 | 6/1991 |
| JP | 10-330745 | 12/1998 |
| JP | 11-278832 | 10/1999 |
| JP | 2000212558 | 2/2000 |
| JP | 2000-212558 | 8/2000 |
| JP | 2001-116699 | 4/2001 |
| WO | WO9407142 | 3/1994 |
| WO | WO9601297 | 1/1996 |

OTHER PUBLICATIONS

Matsuura, Daisuke. Red, Green and Blue Upconversion Luminescence of Trivalent-Rare-Earth Ion-Doped Y2O3 Nanocrystals. Applied Physics Letters, vol. 81, No. 24, Dec. 9, 2002, pp. 4526-4528.*

Semiconductor Nanocrystals as Fluorescent Biological Labels, Marcel Bruchez, Jr., Mario Moronne, Peter Gin, Shimon Weiss, A. Paul Alivisatos, www.sciencemag.org,SCIENCE vol. 281, pp. 2013-2016, Sep. 25, 1998.

Quantum Dot Bioconjugates for Ultrasensitive Nonisotopic Detection, Warren C.W. Chan and Shuming Nie, www.sciencemag.org, SCIENCE, vol. 281, pp. 2016 and 2018, Sep. 25, 1998.

Second Harmonic Generation in Microcrystallite Films of Ultrasmall Si Nanoparticles, M. H. Nayfeh, O. Akcakir, G. Belomoin, N. Barry, J. Therrien, and E. Gratton, Applied Physics Letters, vol. 77, No. 25, pp. 4086-4088, Dec. 18, 2000.

Up-Converting Phosphor Reporters for Nucleic Acid Microarrays, Frans van de Rijke, Henry Zijlmans, Shang Li, Tim Vail, Anton K. Raap, R. Sam Niedbala, and Hans J. Tanke, 2001 Nature Publishing Group http://biotech.nature.com, vol. 19, pp. 273-276, Mar. 2001.

Frans van de Rijke et al, Journal of nature biotechnology, "Up-converting phosphor reporters for nucleic acid microarrays", vol. 19, pp. 273-276 (Mar. 2001).

R. Sam Niedbala et al, Journal of Analytical Biochemistry, "Detection of Analytes by Immunoassay Using Up-Converting Phosphor Technology", vol. 293, pp. 22-30 (2001).

* cited by examiner

*Primary Examiner*—Maureen M Wallenhorst
(74) *Attorney, Agent, or Firm*—Ladas & Parry LLP (57) ABSTRACT

Fine particles whose excitation light is not UV light or the like which has negative effects on a subject to be analyzed. The excitation light is emitted stably, and has excellent light emitting efficiency. Also a fluorescent probe including: fine particles containing a rare earth element excited by light having a wavelength in a range of 500 nm to 2000 nm and thereby emit up-conversion emission; and a specific binding substance which binds to the fine particles containing a rare earth element.

14 Claims, 7 Drawing Sheets

FINE PARTICLES CONTAINING RARE EARTH ELEMENT AND FLUORESCENT PROBE USING THE SAME

TECHNICAL FIELD

The present invention relates to fine particles containing a rare earth element which are excited by red light or infrared light and emit what is called "up-conversion emission" and a manufacturing method of the fine particles. The present invention also relates to a fluorescent probe labeled by the fine particles containing a rare earth element. The fine particles containing a rare earth element and the fluorescent probe of the present invention can suitably be used in the fields of gene diagnosis, immunodiagnosis, medicinal development, environmental testing, biotechnology, a fluorescent inspection, and the like.

BACKGROUND ART

Conventionally, in the fields of medicine and biology, a method in which a fluorescent material composed of organic molecules is used as a marker and fluorescence generated by UV irradiation is measured by an optical microscope or a photo detector. Well-known examples of such a method include an antigen-antibody fluorescent method. In this method, an antibody, to which an organic fluorescent body capable of emitting fluorescence is bound, is used. As the antigen-antibody reaction is extremely highly selective, as is often compared to a relationship between a key hole and a key. Therefore, it is possible to identify the location of the antigen based on the distribution of fluorescence intensity.

As another example, there is a fluorescence-utilizing method using so called DNA chips. When this testing method is employed for a purpose of determining the base sequence of an unknown DNA, the scheme thereof is as follows. That is, by reacting what is called DNA chips in which a large number of DNA (DNA fragments) having known base sequences are arranged in spots-like on a substrate, and DNA having an unknown base sequence which is an organic fluorescent body labeled subject to be tested, the base sequence of the subject is determined by analyzing the position, strength and the like of the fluorescent spots on the DNA chips.

However, the aforementioned conventional organic fluorescent body useful for fluorescent labeling has problems, that is, a problem such that the organic fluorescent body is not stable in storage and at the time of measuring fluorescence, and there is a possibility of deterioration.

In order to solve the problems as describe above, there has been proposed a method of using CdSe nanoparticles ("Semiconductor Nanocrystals as Fluorescent Biological Labels" Marcel Bruchez Jr. et al., p2013-2016, SCIENCE Vol. 281, 25 Sep. 1998; "Quantum Dot Bioconjugates for Ultrasensitive Nonisotopic Detection" Warren C. W. Chan and Shuming Nie. P2016-2018, SCIENCE Vol. 281, 25 Sep. 1998). However, in the above-mentioned method, as the excitation light is blue light or UV light, there arises a problem that, when the subject to be analyzed or detected is a living cell or a living tissue, the excitation light damages the analyzing or detecting subject. Further, when the subject to be analyzed or detected is DNA or a protein, there is a possibility that UV light damages molecules. Therefore, in this method, there is a possibility that determination of base sequences and activity sites with high precision is disturbed.

As particles which emit light by excitation light of a longer wavelengths, Si nanoparticles which emits two-photon excitation have been proposed ("Second harmonic generation in microcrystallite films of ultra small Si nanoparticles" APPLIED PHYSICS LETTERS VOLUME 77, NUMBER 25 18 Dec. 2000). However, as this method is based on a mechanism of light emitting by two-photon absorption, there arises problems in that the light emitting efficiency is poor and the detection precision deteriorates and that super fine particles of no larger than 1 nm are necessary and thus the manufacturing process thereof is complicated.

DISCLOSURE OF THE INVENTION

The present invention has been achieved in consideration of the problems described above. A main object of the present invention is to provide: fine particles whose excitation light is not the one such as UV light or the like which has negative effects on a subject to be analyzed, emit light stably, and has excellent light emitting efficiency; a method for manufacturing the fine particles; and a fluorescent probe labeled with the fine particles.

In order to achieve the aforementioned object, the present invention provides a fine particle containing a rare earth element, characterized in that it is excited by light having a wavelength in a range of 500 nm to 2000 nm and thereby emits up-conversion emission. As the fine particles containing a rare earth element of the present invention are fine particles containing a rare earth element which thus emits up-conversion emission, there is no need to use UV light or blue light as excitation light when the particles are employed as a fluorescent probe. Therefore, there is no possibility of damaging biopolymer to be analyzed. Further, there is no problem of lacking in stability in storage like organic fluorescent body. And further, the fine particles have an advantage of high light emitting efficiency.

In the above mentioned invention, it is preferable that comprising: a core portion containing the rare earth element; and a functional shell portion modifying a surface of the core portion; wherein the functional shell portion comprising at least a specific binding substance binding site which can be bound to a specific binding substance. By comprising such functional shell portion, binding to a specific binding substance is easily possible.

Further, in the above mentioned invention, it is preferable that the specific binding substance binding site is at least one of, a site with condensation reactivity, a site with addition reactivity, a site with substitution reactivity, or a site capable of effecting a specific interaction. Such sites as described above can bind to the specific binding substances more securely.

In the present invention, it is preferable that the fine particles containing rare earth element comprises an agglutinate preventing site which prevents agglutination of the fine particles containing a rare earth element. For example, in the case of being in a liquid having a high salt concentration such as a body fluid, it can be used without agglutination.

In the above mentioned invention, it is preferable that the agglutinate preventing site is at least one of site of, a site having hydrogen bonding, or a site with hydrating ability. By comprising an agglutinate preventing site as described, agglutination of the fine particles containing a rare earth element can reliably be prevented.

Further, it is preferable that the functional shell portion comprises a core portion binding site, which binds to the core portion. By comprising such a core portion binding site, the binding of the core portion and the functional shell portion is made stronger, and inconveniences such as peeling of the functional shell portion from the core portion can be prevented.

Further, it is preferable that the core portion binding site is at least one of, a site with a function to bind to a metal, a site with condensation reactivity, a site with addition reactivity, or a site with substitution reactivity. By comprising the site as described, binding of the core portion and the functional shell portion can be conducted more securely.

In the above mentioned invention, it is preferable that the average particle diameter of the core portion is in a range of 1 to 100 nm. It is because when polynucleotide, an antigen, an antibody or the like is used as a specific binding substance, the average particle diameter in the aforementioned range is preferable.

Moreover, it is preferable that the core portion is made of a halide or an oxide as a parent material, and comprises a rare earth element which can emit the up-conversion emission. When a halide is used as a parent material, it is advantageous because an excellent light emitting efficiency is obtained. When an oxide is used as a parent material, it is advantageous because resistance to environmental conditions, e.g., waterproof, is high and thus stable light emitting can be obtained.

In the present invention, it is preferable that the rare earth element is at least one of rare earth element selected from the group consisting of erbium (Er), holmium (Ho), praseodymium (Pr), thulium (Tm), neodymium (Nd), gadolinium (Gd), europium (Eu), ytterbium (Yb), samarium (Sm) and cerium (Ce). As rare earth elements capable of emitting up-conversion emission, these are preferable.

In the above mentioned invention, the fine particle containing a rare earth element can be formed from a fine particle of 1 to 100 nm average particle diameter of the oxide doped whit the rare earth element. The oxide is preferably at least one of oxide selected form the group consisting of yttrium oxide, gadolinium oxide, lutetium oxide, lanthanum oxide and scandium oxide. This is because as the oxides doped with the rare earth element, these are preferable.

A fluorescent body is used, in most cases, in powdery form. The average particle diameter of the fluorescent body is in a range of approximately 3 to 12 μm. When the particle diameter is reduced, the light emitting efficiency starts to decrease below a certain particle diameter (approximately 1 to 2 μm, although it depends on the type of the material). It is assumed that it is due to the light emitting efficiency at a surface layer of crystal is low.

In 1994, it was reported that a high light emitting efficiency is obtained in fluorescent particles having particle diameter of a few to several dozrn nm, and attracted attention ("Optical Properties of Manganese-Doped Nanocrystals of ZnS" APPLIED PHYSICS LETTERS, VOLUME 72, NUMBER 317, JANUARY, 1994). This phenomenon was explained on the basis of and confining emit of excitons.

Therefore, by setting the particle diameter of the fine particles containing a rare earth element at approximately 100 nm or less, the light emitting efficiency of up-conversion emission by the fine particles containing a rare earth element is likely to be further enhanced.

The presence of fine particles containing a rare earth element, whose particle diameter is approximately 100 nm or less, cannot be visually confirmed, unless the fine particles containing a rare earth element is emitting light. Therefore, they are suitable as a marker for a fluorescent test, such as a marker for telling the real from the false of a holographic element.

In the present invention, erbium and ytterbium can be used as the above-mentioned rare earth element. By regulating the amounts to be added of these two types of rare earth elements, the visually-perceived color of the light emitted from the fine particles containing a rare earth element, as a result of the up-conversion, can be controlled within a wavelength range from green to red.

Furthermore, erbium may be used as the above-mentioned rare earth element. By doping yttrium oxide with erbium, the fine particles containing a rare earth element which emits green fluorescence by up-conversion can be obtained.

Alternatively, thulium and ytterbium can be used as the above-mentioned rare earth element. When thulium and ytterbium are added, sensitive to light in the near infrared region can be obtained, whereby it becomes possible to induce blue light by excitation light in the near infrared region.

In the above invention, the aforementioned fine particles containing a rare earth element can be manufactured by a method for manufacturing a fine particle containing a rare earth element comprising: a first process of doping the rare earth element to at least one kind of basic carbonate selected from the group consisting of basic yttrium carbonate, basic gadolinium carbonate, basic lutetium carbonate, basic lanthanum carbonate and basic scandium carbonate; and a second process of calcination of the basic carbonate doped with the rare earth element.

Moreover, it is preferable that, the basic carbonate doped with the rare earth element is obtained by a liquid phase reaction, in the first process. When the basic carbonate is obtained by a liquid phase reaction, fine particles containing a rare earth element having a small particle diameter can be obtained more easily.

In the above mentioned invention, it is preferable that, at least one kind of nitrate selected from the group consisting of yttrium nitrate, gadolinium nitrate, lutetium nitrate, lanthanum nitrate and scandium nitrate; a nitrate of the rare earth element to be doped; and sodium carbonate, are reacted in the first process. When these are reacted in a liquid phase, the aforementioned basic carbonate can be obtained more easily.

Further, it is preferable that the basic carbonate doped with the rare earth element is quenched after calcination by a rapid heating, in the second process. By calcination by rapid heating and then rapidly cooling, the fine particles containing a rare earth element, whose particle diameter is small, can be obtained easily.

In the above mentioned invention, it is preferable that the rare earth element is selected depending on the wavelength of the desired fluorescence. As described above, the wavelength of the up-conversion emission from the fine particles containing a rare earth element changes depending on the type of the rare earth element which is to be doped on an oxide. Accordingly, it is advantageous, in practical terms, to obtain the up-conversion emission whose wavelength is suitable for the application of the fine particles containing a rare earth element.

The present invention also provides a fluorescent probe comprising: the above mentioned fine particle containing a rare earth element; and a specific binding substance which binds to the fine particle containing a rare earth element. Such a fluorescent probe has the advantage of the fine particles containing a rare earth element, i.e., it is not necessary to use UV light or blue light as excitation light. Thus, it dose not damage the biopolymer as the subject to be analyzed, does not cause problems such as lack of stability in storage like an organic fluorescent body, and has an advantage of high light emitting efficiency.

In the present invention, it is preferable that the above mentioned specific binding substance is any one of, polynucleotide, hormone, protein, antigen, antibody, peptide, cell or tissue. The present invention is unique in that red light or infrared light which is less likely to damage biopolymer is used as excitation light. Particularly in these above mentioned substances, damage by the excitation light is likely to be a problem.

BEST MODE FOR CARRYING OUT THE INVENTION

Hereinafter, the fine particles containing a rare earth element and a fluorescent probe using the same will be described in detail.

A. Fine Particles Containing a Rare Earth Element

The fine particles containing a rare earth element of the present invention are characterized in that they are excited by light having a wavelength in a range of 500 to 2000 nm and thereby emit up-conversion emission.

Figure 1A:
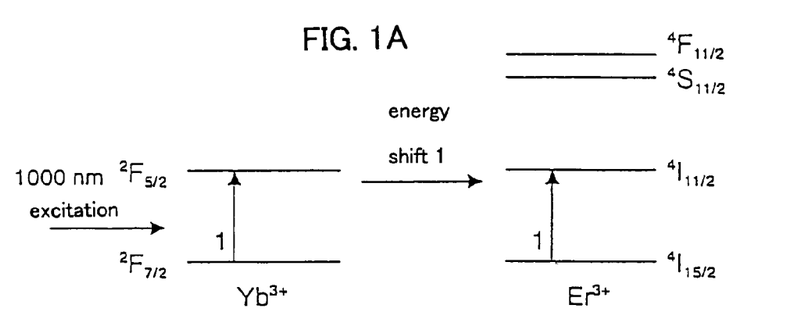
FIG. 1 is an explanatory diagram for explaining up-conversion emission.
Figure 1B:
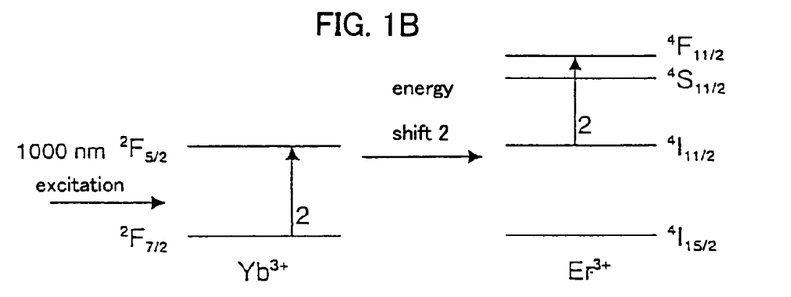
Figure 1C:
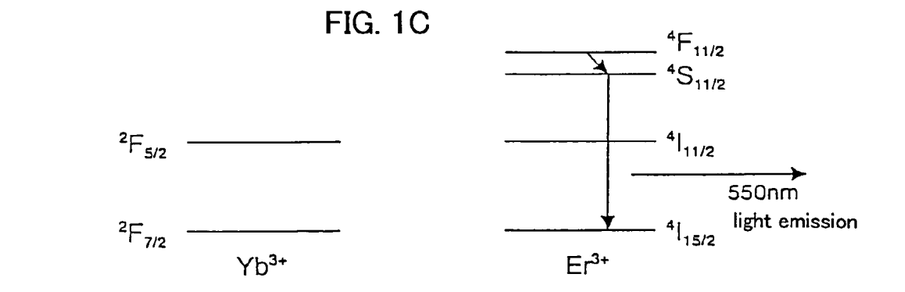

First, the up-conversion emission utilized in the present invention will be described with reference to FIG. 1. In FIG. 1, one example, which is a system using two types of rare earth elements, i.e., ytterbium (Yb) and erbium (Er) as the rare earth element, and in which infrared light of 1000 nm has been irradiated as excitation light, is shown. As shown in FIG. 1A, ytterbium ($Yb^{3+}$) is first excited by excitation light of 1000 nm, thereby being shifted from $^2F_{7/2}$ level to $^2F_{5/2}$ level which is higher in energy level. This energy then pushes up, due to the energy transfer 1, the energy level of erbium ($Er^{3+}$) from $^4I_{15/2}$ level to $^4I_{11/2}$ level. Thereafter, as shown in FIG. 1B, ytterbium ($Yb^{3+}$) is excited by excitation light of 1000 nm and this energy pushes up, due to the energy shift 2, the energy level of erbium ($Er^{3+}$) from $^4I_{11/2}$ level to $^4F_{11/2}$ level. Then, as shown in FIG. 1C, the above mentioned excited erbium ($Er^{3+}$) emits light of 550 nm when returning to the ground state.

Thus, when a substance excited by light of 1000 nm emits light of 550 nm, having higher energy, that is, in terms of wavelength, when an excited substance emits light having higher energy than the excitation light, such light emitting is referred to as "up-conversion emission".

Figure 2:
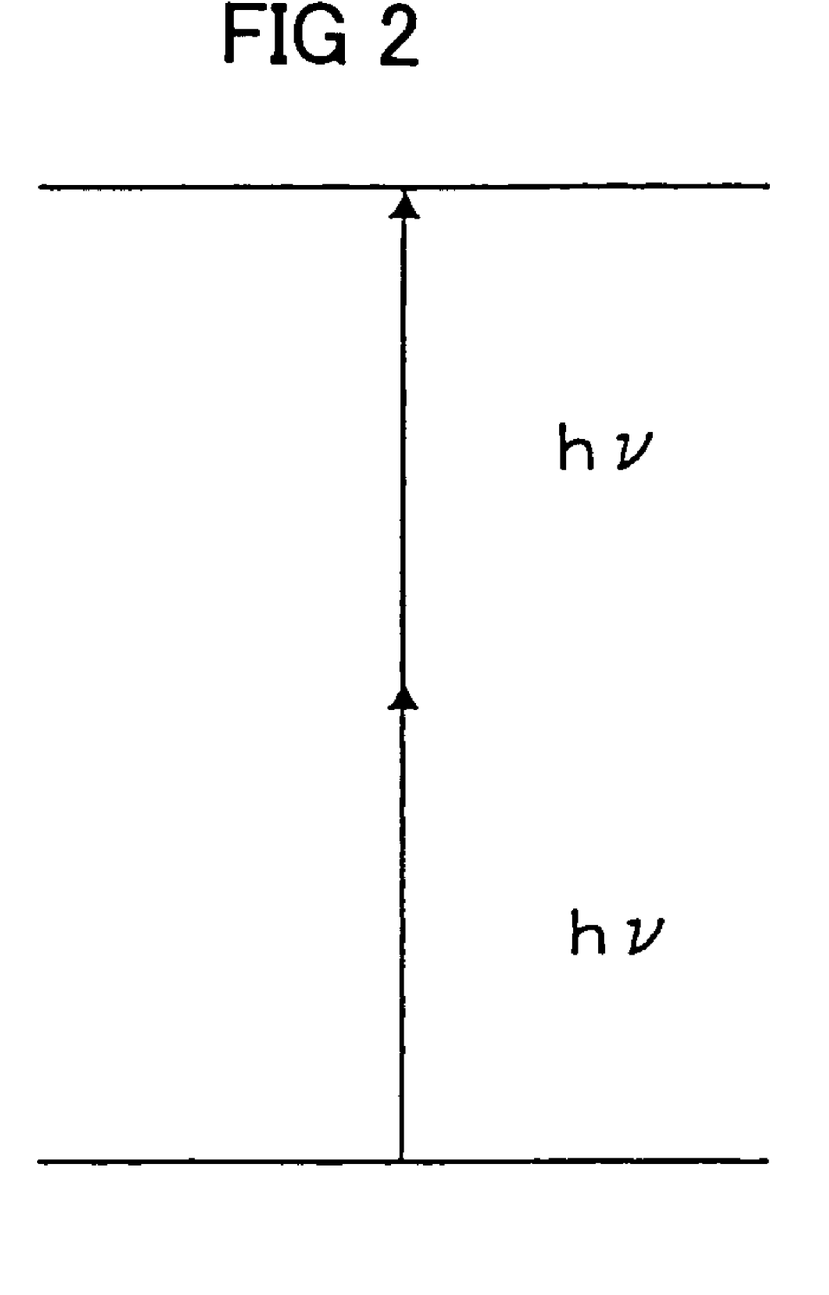
FIG. 2 is an explanatory diagram for explaining two-photon light emitting.

The Si nanoparticles, described in the aforementioned Background Art, which cause two-photon excitation is excited only when two photons are absorbed at the same time, as shown in FIG. 2, and is different in principle from the above-mentioned up-conversion emission. This two-photon excitation has poor light emitting efficiency because two photons must exist simultaneously. On the contrary, the up-conversion emission is free of such requirements and has extremely high light emitting efficiency, as compared with the Si nanoparticles which cause two-photon excitation.

In the present invention, since a rare earth element which emits the aforementioned up-conversion emission is employed, there is no need for excitation by light having high energy such as UV light. That is, the wavelength of light when emitting light is preferably, in general, the visible light so that analysis or detection thereof is easy. Therefore, for up-conversion emission, light having a longer wavelength than visible light is used as excitation light. As a result, UV light or blue light which is likely to damage biopolymer is prevented from being used as excitation light. Further, as the wavelength of the excitation light and the wavelength of the emitted light are hardly overlapped, analysis or detection is significantly facilitated.

As described above, as the fine particles containing a rare earth element of the present invention employ a rare earth element which can emit up-conversion emission, the excitation light does not damage the subject to be analyzed and thus an accurate analysis can be done. Further, the light emitting efficiency is much higher than the two-photon excitation and the stability during storage is excellent, as compared with the case of using the organic fluorescent body. Thus, a stable and highly precise analysis can be done.

The fine particles containing a rare earth element of the present invention, which contain a rare earth element capable of emitting such up-conversion emission, for example, may be constituted from a core portion containing the rare earth element capable of emitting the up-conversion emission, and a functional shell portion having a function of being bound to a specific binding substance and preventing agglutination (hereinafter, the fine particles containing a rare earth element of this type will be referred to as "first fine particles containing a rare earth element"). Alternatively, they may be constituted from an oxide doped with a rare earth metal having average particle diameter of 1 to 100 nm and (hereinafter, such fine particles containing a rare earth element will be referred to as "second fine particles containing a rare earth element").

Hereinafter, the fine particles containing a rare earth element of the present invention will be described, first on the first fine particles containing a rare earth element and then on the second fine particles containing a rare earth element.

(I) First Fine Particles Containing a Rare Earth Element

The diameter of the first fine particles containing a rare earth element as a whole is preferably in a range of 1 to 500 nm, and especially preferably in a range of 1 to 100 nm. A surface of such first fine particles containing a rare earth element, i.e., the functional shell portion, is preferably provided with a functional group. By this, binding with a specific binding substance is facilitated.

The first fine particles containing a rare earth element as described above, of the present invention, will be described in detail, first on the core portion and then on the functional shell portion.

1. Core Portion

The core portion of the first fine particles containing a rare earth element of the present invention contains a rare earth element. First, such rare earth element will be described, followed by the description of the core portion containing the rare earth element.

(1) Rare Earth Element

The rare earth element used in the present invention is not particularly limited as long as it is a rare earth element, which is excited by light having a wavelength in a predetermined range, as describe above, and can thereby emit up-conversion emission.

With regards to the range of the wavelength of the excitation light, the wavelength needs to be at least in a range of 500 to 2000 nm, preferably in a range of 700 to 2000 nm, and particularly preferably in a range of 800 to 1600 nm, so that the excitation light does not damage biopolymer.

Examples of such a rare earth element generally include a rare earth element which can be a trivalent ion. Specifically, rare earth elements such as erbium (Er), holmium (Ho), praseodymium (Pr), thulium (Tm), neodymium (Nd), gadolinium (Gd), europium (Eu), ytterbium (Yb), samarium (Sm) and cerium (Ce) can be suitably used.

In the present invention, the rare earth element capable of up-conversion emission as described above may be used either as a single type of element or as a combination of two or more types of elements at a time. The mechanism of up-conversion emission when a single type of a rare earth element is used, explained using $Er^{3+}$ dope material as an example is as follows: when light of 970 nm or 1500 nm is irradiated as excitation light, followed by the up-conversion process, visible light of such as 410 nm ($^2H_{9/2}$-$^4I_{15/2}$), 550 nm ($^4S_{3/2}$-$^4I_{15/2}$), 660 nm ($^4F_{9/2}$-$^4I_{15/2}$) is emitted in accordance with the energy level of $Er^{3+}$ ion.

(2) Core Portion

The the core portion containing a rare earth element is not particularly limited as long as the core portion contains the rare earth element therein in a state in which up-conversion emission can be emitted, and the core portion may be an organic matter, for example, such that formed in a state of comprising the rare earth element in a complex, a dendrimer, or the like. However, the core portion formed by mixing the aforementioned rare earth elements in an inorganic parent material is generally preferable because, it is easy to make the rare earth element contained in a state that can emit light.

As the inorganic parent material, a material which has transparency to excitation light is preferable in terms of light emitting efficiency. Specifically, a halide such as a fluoride and a chloride, an oxide, a sulfide and the like can be suitably used.

In the present invention, a halide is suitably used in terms of light emitting efficiency. Specific examples of such a halide include barium chloride ($BaCl_2$), lead chloride ($PbCl_2$), lead fluoride ($PbF_2$), cadmium fluoride ($CdF_2$), lanthanum fluoride ($LaF_3$), yttrium fluoride ($YF_3$) and the like. Among these examples, barium chloride ($BaCl_2$), lead chloride ($PbCl_2$) and yttrium fluoride ($YF_3$) are preferable.

As an example of the parent material with high environmental resistance such as being stable to moisture, an oxide can be raised. Specific examples of such an oxide include yttrium oxide ($Y_2O_3$), aluminum oxide ($Al_2O_3$), silicon oxide ($SiO_2$), tantalum oxide ($Ta_2O_5$), and the like. Among these examples, yttrium oxide ($Y_2O_3$) is preferable.

When a halide is used as the parent material, it is preferable that a protection layer is formed around. A halide is generally unstable to water and the like, and if halide particles are used as they are, analysis may not be done accurately. In such cases, it is preferable that the core portion is formed as a composite core portion, which comprises a coating material having waterproof ability or the like formed around fine particles made of a halide as the parent material. As the coating material in such cases, the oxide as described above can be suitably used.

Examples of a method of introducing a rare earth element to a parent material include: in a case of a halide such as barium chloride ($BaCl_2$), methods described in JP-A 9-208947 Laid-Open or a reference ("Efficient 1.5 mm to Visible Upconversion in $Er^{3+}$ Doped Halide Phoshors" Junichi Ohwaki et al., p. 1334-1337, JAPANESE JOURNAL OF APPLIED PHYSICS, Vol. 31 part 2 No. 3A, 1 Mar. 1994). In a case of an oxide, methods described in JP-A 7-3261 Laid-Open or references ("Green Up conversion Fluorescence in $Er^{3+}$ Doped $Ta_2O_5$ Heated Gel" Kazuo Kojima et al., Vol. 67(23), 4 Dec. 1995; and "Relationship Between Optical Properties and Crystallinity of Nanometer $Y_2O_3$: Eu Phoshor" APPLIED PHYSICS LETTERS, Vol. 76, No. 12, p. 1549-1551, 20 Mar. 2000).

In the present invention, the amount of the rare earth element to be introduced in the above mentioned parent material changes significantly depending on the type of the rare earth element, the type of the parent material, or the desired degree of intensity of light emitting. Therefore, the amount is set in an appropriate manner, in consideration of the various conditions.

The average particle diameter of the core portion is preferably in a range of 1 to 100 nm and more preferably in a range of 1 to 50 nm. Synthesis of fine particles with average particle diameter of the core portion of less than 1 nm would be extremely difficult and thus not preferable. On the other hand, fine particles with average particle diameter of the core portion exceeding 100 nm tend to disturb the reaction of the subject to be labeled, the specific binding substance, thereby deteriorating the precision of data, thus not preferable.

The color of the emitting light of the up-conversion emission of the rare earth elements differs depending on the composition. Therefore, by utilizing this feature, by labeling plural types of specific binding substances having different specificity, with different color light emitting fine particles containing a rare earth element respectively, and conducting the same measurement, it is possible to detect different types of testing substances simultaneously.

2. Functional Shell Portion

The first fine particles containing a rare earth element of the present invention has the functional shell portion formed around the core portion. The functional shell portion is required not to be agglutinated in a liquid having a relatively high salt concentration such as body fluid, and not to perform an on-specific reaction in a sample liquid.

The specific characteristics which are required to such functional shell portion, first, having binding ability to a specific substance can be pointed out. That is, it is preferable that the functional shell portion has a specific binding substance binding site, which is the site binds to a specific binding substance and it is preferable that the functional shell portion is formed of a material comprising such sites.

Such a specific binding substance binding site as described above is not particularly limited as long as the site provide physical binding capacity or chemical binding capacity to a surface of the shell portion. Specific examples thereof include a site with ion dissociation ability, a site with ion coordination ability, a site with a function to bind to a metal, a site with condensation reactivity, a site with addition reactivity, a site with substitution reactivity, a site with hydrogen bonding ability, and a site capable of effecting a specific interaction. Among these examples, the site is preferably at least one of a site with condensation reactivity, a site with addition reactivity, a site with substitution reactivity, and a site capable of effecting a specific interaction.

Specific examples of such a preferable binding site include carboxyl group, amino group, hydroxyl group, aldehyde group (—CHO), vinyl group ($CH_2$=CH—), acryloyl group, methacryloyl group, epoxy group, acetal group (($CH_3CH_2O)_2$ CH—), an imide site and a biotin site.

Next, as characteristic which is required to the functional shell portion is that the functional shell portion is capable of preventing the first fine particles containing a rare earth element from agglutination. Accordingly, it is preferable that the functional shell portion has an agglutinate preventing site which prevents the first fine particles containing a rare earth element from agglutination, and is formed of a material comprising such sites.

The agglutinate preventing site is preferably at least one of a site of a site having hydrogen bonding or a site with hydrating ability. Specific examples thereof include ethylene oxide site (—($CH_2CH_2O)_n$—) (n is an integer in a range of 2 to 10,000), hydroxyl group (—OH), amide site (—CONH—), phosphate ester site (—$PO(OR)_n(OH)_{3-n}$, (n is 1, 2 or 3, R represents a hydrocarbon-containing group having 2 or more carbon atoms)) and a betaine site. It is especially preferable that the agglutinate preventing site is one of an ethylene oxide site (—($CH_2CH_2O)_n$—) (n is an integer in a range of 2 to 10,000) typically represented by polyethylene glycol, or betaine site, because they excel in function to form a stable hydration layer on the surface of the fine particles and excel in function to prevent agglutination or non-specific adsorption.

Other preferable examples of the site with agglutinate preventing function include an ion-dissociation site which effects electrostatic repulsion. Specific examples thereof include carboxyl group, sulphonic group, amino group, imino group, betaine group. A polymer comprising these groups is especially preferable, because such a polymer excels in functions to form a stable electrostatic repulsion layer on the surface of the fine particles.

Further, in the present invention, it is preferable that the functional shell portion comprises a core portion binding site, which binds to the core portion, therefore, it is preferable that it is formed of a material comprising such sites. Such site may include at least one of a site with a function to bind to a metal, a site with condensation reactivity, a site with addition reactivity, and a site with substitution reactivity.

Specific examples include methoxysilyl group (—Si($OCH_3)_nY_{n-1}$ (n is 1, 2 or 3, Y represents methyl or ethyl)), ethoxysilyl group (—Si($OCH_2CH_3)_nY_{n-1}$ (n is 1, 2 or 3, Y represents methyl or ethyl)), propoxysilyl group (—Si($OC_3H_7)_nY_{n-1}$ (n is 1, 2 or 3, Y represents methyl or ethyl)), chlorosilyl group (—Si$Cl_nY_{n-1}$ (n is 1, 2 or 3, Y represents methyl or ethyl)), vinyl group, acryloyl group, methacryloyl group and the like.

Further, it is preferable that the functional shell portion is formed of a material with a function to prevent deterioration of light emitting efficiency of the first fine particles containing a rare earth element, due to non-radiation, a chemical reaction, or other causes. Also, a material which firmly coordinates or binds to the surface of the core portion of the first fine particles containing a rare earth element is preferable. It is especially preferable that such a material is polymerizable. That is, materials having a site with ion coordination ability, a site with a function to bind to a metal, a site with condensation reactivity, a site with addition reactivity, or a site with substitution reactivity are preferable. Specific examples thereof include materials comprising carboxyl group, amino group, imino group, thiol group, Schiff base site (—CH=N—), methoxysilyl group (—Si($OCH_3)_nY_{n-1}$ (n is 1, 2 or 3, Y represents methyl or ethyl)), ethoxysilyl group (—Si($OCH_2CH_3)_nY_{n-1}$ (n is 1, 2 or 3, Y represents methyl or ethyl)), propoxysilyl group (—Si ($OC_3H_7)_nY_{n-1}$ (n is 1, 2 or 3, Y represents methyl or ethyl)), chlorosilyl group (—Si$Cl_nY_{n-1}$ (n is 1, 2 or 3, Y represents methyl or ethyl)), vinyl group, acryloyl group, methacryloyl group and the like.

As described above, the functional shell portion is required to have various functions. Therefore, as materials forming such functional shell portion, a material having the above mentioned desired functions as a complex is preferable. Chemical formulae of specific examples of such a preferable material are shown below.

-continued

3. Method for Manufacturing the First Fine Particles Containing a Rare Earth Element Examples of a method for manufacturing the core portion of the first fine particles containing a rare earth element include: the evaporation-in-gas method including the high frequency plasma method; spattering method; glass crystallization method; chemical precipitation method; the reverse micelle method; the sol-gel method and equivalent methods thereof; precipitation method including hydrothermal synthesis method and coprecipitation method; and spraying method.

Preferable examples of a method of forming the functional shell portion on the surface of the core portion of the first fine particles containing a rare earth element include: a method of forming covalent bond of the functional group of the material constituting the functional shell portion, with the functional group of the core portion surface, by a condensation or addition reaction; a method of synthesizing the functional shell portion in the presence of the core portion by the sol-gel method or an equivalent method thereof; and a method of making the core portion adsorb a precursor of the functional shell portion and then polymerizing. When the core portion is synthesized by chemical precipitation method, the reverse micelle method, the sol-gel method or an equivalent method thereof, it is possible to utilize a surfactant or a protecting agent used at the time, as the shell portion or the precursor of the shell portion.

(II) Second Fine Particles Containing a Rare Earth Element

1. Second Fine Particles Containing a Rare Earth Element

The second fine particles containing a rare earth element are fine particles having average particle diameter of 1 to 100 nm and comprising an oxide as a parent material doped with a rare earth element. The second fine particles containing a rare earth element correspond to one preferable embodiment of the core portion of the above mentioned first fine particles containing a rare earth element. However, the second fine particles containing a rare earth element are different from the first fine particles containing a rare earth element in that the functional shell portion is not an essential component.

The oxide used as the parent material may be selected from the group comprising yttrium oxide, gadolinium oxide, lutetium oxide, lanthanum oxide and scandium oxide. The number of oxide may be of either a single type or two or more types of the aforementioned examples.

The rare earth element to be doped with on the parent material may be either of a single type or two or more types of the rare earth elements according to the wavelength of the desired up-conversion emission.

For example, in a case in which yttrium oxide is doped with erbium, the second fine particles containing a rare earth element, which emit green light as a result of up-conversion caused by excitation by light having a wavelength of 980 nm, can be obtained.

Alternatively, in a case in which yttrium oxide is doped with erbium and ytterbium, the second fine particles containing a rare earth element, which emits light of a predetermined color within the wavelength range of green to red, in a visually recognizable manner as a result of up-conversion caused by excitation by light having a wavelength of 980 nm, can be obtained. For example, when erbium is added by the amount of 1 mol % and ytterbium is added by the amount of 20 mol %, the second fine particles containing a rare earth element, which emits red light in a visually recognizable manner by excitation by light having a wavelength of 980 nm, can be obtained.

Figure 7:
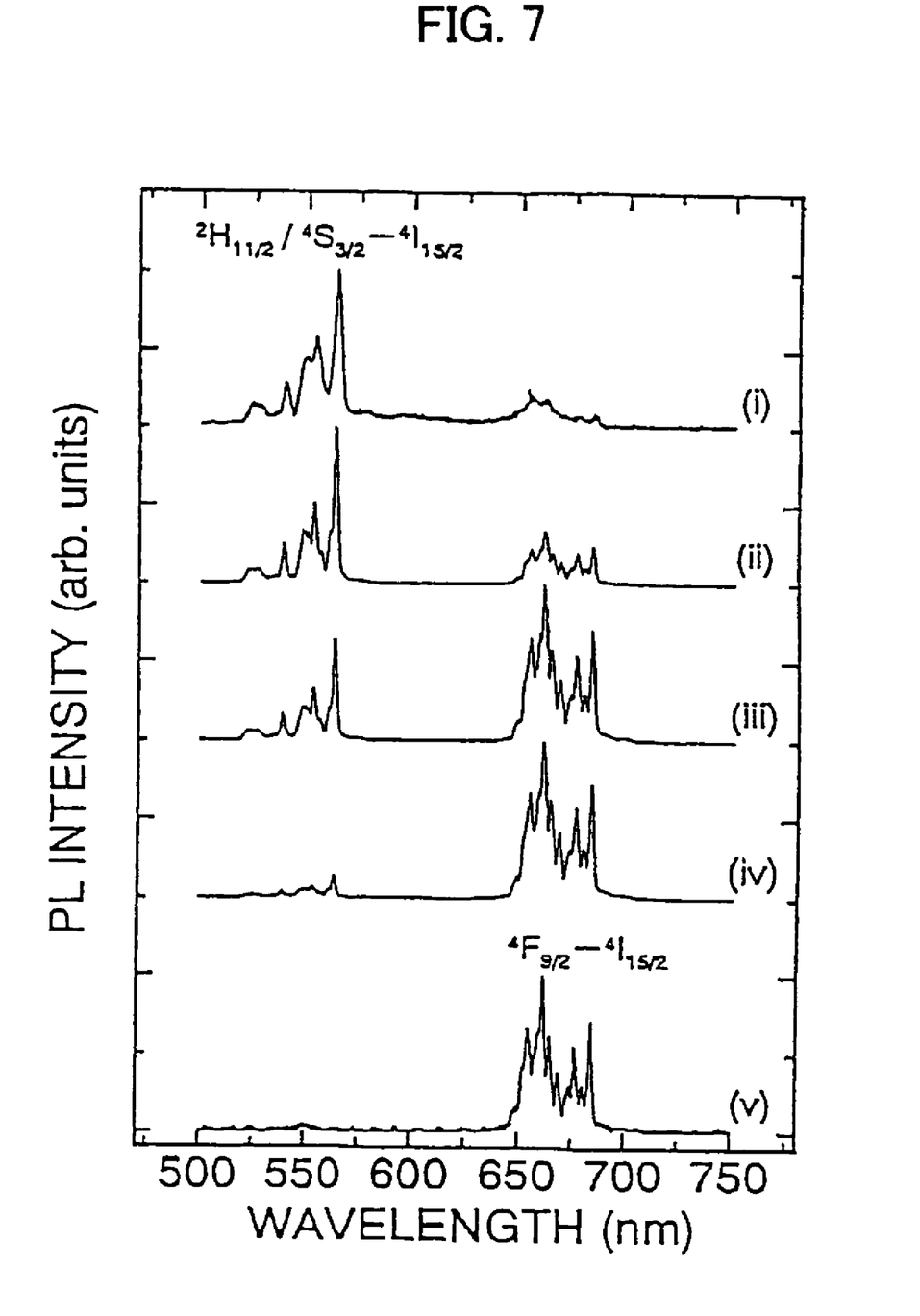
FIG. 7 is a graph showing light emitting spectrum resulting from excitation by semiconductor laser (980 nm) of the fine particles containing a rare earth element, which are obtained by fixing the amount of erbium to be added to yttrium oxide at 1 atom %, while changing the amount of ytterbium to be added to 0 atom %, 1 atom %, 3 atom %, 5 atom % and 20 atom %, respectively.

FIG. 7 shows spectra of fluorescence by up-conversion, obtained from the second fine particles containing a rare earth element obtained by fixing the content of erbium added to yttrium oxide at 1 atom % while changing the content of ytterbium added at 0 atom %, 1 atom %, 3 atom %, 5 atom % and 20 atom %, respectively. In FIG. 7, spectra at 0 atom %, 1 atom %, 3 atom %, 5 atom % and 20 atom % of the added yttrium amount are shown as spectrum (i) to (iv), respectively, in this order.

As is obvious from FIG. 7, the color of light which is visually recognized when the second particles containing a rare earth element is excited changes within the wavelength range of green to red, in accordance with the ratio of the adding amount of erbium and ytterbium.

In a case of yttrium oxide is doped with thulium and ytterbium, as the sensitivity to light in the near infrared region is increased by ytterbium, light emitting of blue light due to thulium can be obtained with higher intensity when excited by light having a wavelength of 980 nm.

The amount of a rare earth element to be added to ytterbium oxide at the time maybe appropriately selected within in a certain range which concentration quenching dose not occur. For example, when erbium, ytterbium, or thulium are added to yttrium oxide, the added amount of erbium, ytterbium and thulium maybe selected, respectively, in an appropriate manner within a range of 0 to 50 mol %.

2. Method for Manufacturing the Second Fine Particles Containing a Rare Earth Element The aforementioned second fine particles containing a rare earth element can be obtained, for example, by: preparing a basic carbonate doped with a desired rare earth element; calcination of the basic carbonate; and the then optionally adjusting the particle diameter of the particles to a predetermined size.

The above-mentioned basic carbonate may be selected from the group comprising basic yttrium carbonate, basic gadolinium carbonate, basic lutetium carbonate, basic lanthanum carbonate and basic scandium carbonate. The number of the basic carbonate may be of either a single type or two or more types of the aforementioned examples.

The type of the rare earth element doped on the basic carbonate may be appropriately selected, as describe above, in accordance with the target wavelength of fluorescence to be emitted from the second fine particles containing a rare earth element as a result of up-conversion.

In order to obtain the second fine particles containing a rare earth element having average particle diameter of 1 to 100 nm, it is preferable that the basic carbonate doped with the desired rare earth element is obtained by a liquid phase reaction. Such a basic carbonate can be obtained by reacting a nitrate of a metal which is a component element of the basic carbonate to be doped with a rare earth element, with a nitrate of the rare earth element used to bedoped, and sodium carbonate.

When a basic carbonate doped with the desired rare earth element is calcined, it is preferable that the calcination is carried out by rapid heating, followed by rapid cooling. By heating rapidly and then cooling rapidly, growth of particles is prevented and the average particle diameter can be made no larger than 100 nm.

In the present invention, "rapid heating" represents putting in an oven set in a range of 300 to 1700° C., preferably in a range of 500 to 1100° C. for at least 10 minutes, preferably for 30 to 180 minutes. "Rapid cooling" represents taking out of the above mentioned oven and leaving at a temperature condition which is at least 200° C., preferably 500 to 1100° C. lower than the temperature inside the oven.

By going through each of the aforementioned processes, the second fine particles containing a rare earth element as described above can be obtained.

The aforementioned second fine particles containing a rare earth element may be used as the core portion of the above mentioned first fine particles containing a rare earth element.

B. Fluorescent Probe

The fluorescent probe of the present invention comprising: the above mentioned first or second fine particles containing a rare earth element; and a specific binding substance which binds to the above mentioned first or second fine particles containing a rare earth element.

1. Specific Binding Substance

In the present invention, fluorescent probes having various functions can be produced by labeling a known or unknown specific binding substance with the aforementioned first or second fine particles containing a rare earth element. For example, by labeling a known antibody, a fluorescent probe, for analyzing the position of an antigen in a sample to be tested, can be produced. Or, by labeling an unidentified DNA (a sample to be tested), a fluorescent probe, for determining the base sequence of the sample by using DNA chips, can be produced.

Examples of the specific binding substance as described above include synthetic nucleic acid such as deoxyribonucleic acid (DNA), ribonucleic acid (RNA), peptide nucleic acid (PNA); hormone, protein, peptide, cell, tissue, antigen, antibody, receptor, hapten, enzyme, nucleic acid, medical agent, chemical substances, polymer, pathogen, toxin, adenine derivative, guanine derivative, cytosine derivative, thymine derivative, urasil derivative and the like.

In the present invention, synthetic nucleic acid such as deoxyribonucleic acid (DNA), ribonucleic acid (RNA) and peptide nucleic acid (PNA), hormone, protein, antigen, antibody, peptide and cell, of the aforementioned examples, are preferably used as the specific binding substance. As described above, the key feature of the present invention lies in that excitation light does not damage biopolymer. Since even a very slight damage on DNA, RNA, synthetic nucleic acid, hormone, protein, antigen, antibody, peptide and cell by excitation could have a significant impact on the result of the analysis, the present invention is most advantageously applied to such biopolymer.

2. Labeling of Specific Binding Substance by Fine Particles Containing Rare Earth Element In the present invention, a fluorescent probe is produced by labeling the above-mentioned specific binding substance by binding with the above mentioned first or second fine particles containing a rare earth element.

The manner of binding the fine particles containing a rare earth element and the specific binding substance is not particularly limited, and examples of thereof include: physical bonding such as ionic bonding, coordinate bonding and hydrogen bonding; chemical bonding, i.e., covalent bonding; and bonding by a specific interaction. In order to improve the precision in analysis, it is preferable that the specific binding substance is firmly bound to the fine particles containing a rare earth element. Therefore, it is preferable that they are bonded by covalent bond or by a specific interaction.

3. Analyzing or Detecting Method

Examples of the analyzing or detecting method using the fluorescent probe of the present invention include a method using an antigen-antibody reaction, as described below.

Figure 3:
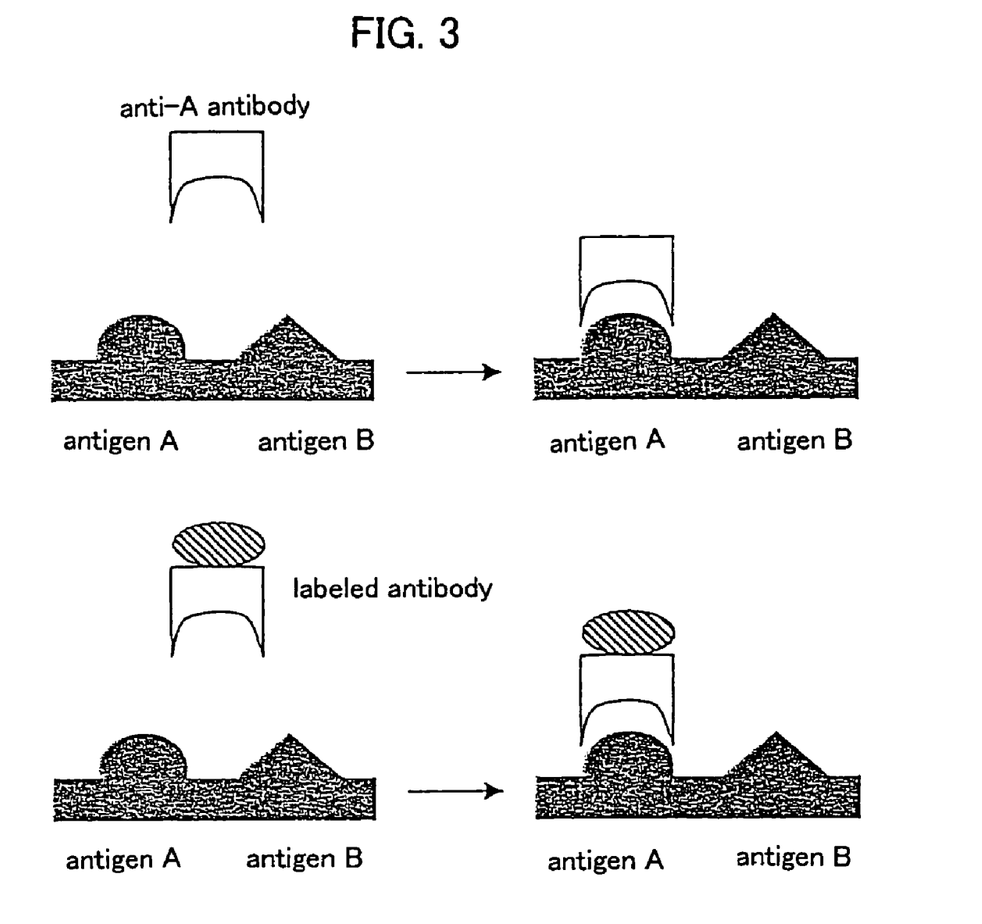
FIG. 3 is a schematic diagram for explaining an usage embodiment of the present invention in an antigen-antibody reaction.

That is, when an antibody is reacted with a substance (antigen) on or inside a cell, the antibody is firmly bound to the antigen as a result of an antigen-antibody reaction. Accordingly, the location of the antigen can be identified based on the binding site. However, in general, the antibody molecule itself can not be observed by a microscope. Thus, it is necessary to label the antibody to be used for antigen detection, with an observable marker in advance. An antigen-antibody reaction is a reversible bonding reaction, as shown, for example, in FIG. 3. The reaction is very specific and the antibody is not reacted with any substance other than the corresponding antigen substance. The upper part of the figure shows that, when antibody is reacted to the tissue sample, the antibody is reacted with and bound to only to antigen A. However, in this state, the location of the antigen cannot be identified because the antibody itself cannot be dyed out. Therefore, as the case shown in the lower part of the figure, when a visually observable marker is bound to the antibody in advance and reacted with the antigen in the tissue, the binding similar to that shown in the upper part of the figure occurs. In this case, the location where the antigen-antibody reaction occurred is indicated by the marker, whereby the site where the antigen is present can be identified. What is important about the labeled antibody is that the ability to be bound to the antigen is not lost by labeling, does not have any non-specific affinity with other substances, and the activity of the marker is sufficiently maintained.

The fluorescent antibody method (fluorescent-labeled antibody method) as described above, is one of the immunohistochemical methods, in which a fluorescent colorant is used as a marker of antibody and the location of antigen is determined by observing the fluorescence emitted as a result of excitation under a fluorescence microscope. This method was first to be established among the immunohistochemical methods, Coons et al. started the development thereof in the early 1940's, and substantially established in 1950's. Thereafter, due to the improvement of the labeling method by Riggs et al. and introduction of the method of purifying labeled antibody by McDvitt et al., the area to which this method is applicable has been widened, and now, this method is one of the most common methods in immunohistochemistry.

The present invention is applicable to the aforementioned method, by employing the first or second fine particles containing a rare earth element, comprising the rare earth element, as the marker, and by making the antibody as the specific binding substance.

As above, by binding a specific binding substance, which specifically binds to another biopolymer, to the aforementioned fine particles containing a rare earth element and thus labeling, various types of analysis and detection are possible.

Examples of such specific binding include: combination of a nucleic acid (for example, oligonucleotide or polynucleotide) and another nucleic acid complementary thereto; combination of antigen and antibody (or antibody fragment) as described above; combination of a receptor and ligand thereof (for example, hormone, cytokinin, neurotransmitter or lectin); combination of an enzyme and ligand thereof (for example, substrate analog of the enzyme, coenzyme, a regulating factor, or an inhibitor); combination of enzyme analog and a substrate of enzyme which is the base of the enzyme analog; and combination of lectin and saccharide. Note that the "enzyme analog" refers to a substance which has significantly high specific affinity to the substrate of the corresponding original enzyme, but exhibits no catalytic activity. Further, the each compound in each of the combinations described above, respectively, either one can be "the specific binding substance", and the other can be the substance to be analyzed or detected. For example, in "the combination of antigen and antibody", when the antigen serves as "the substance to be analyzed or detected", the antibody can be "the specific binding substance". Conversely, when the antibody serves as "the substance to be analyzed or detected", the antigen can be "the specific binding substance".

For example, in a case in which the fluorescent probe of the present invention is applied to a nucleic acid hybridization assay, an oligonucleotide or a polynucleotide, capable of complementarily being bound to a nucleic acid (for example, an oligonucleotide or a polynucleotide) which is a substance to be analyzed or detected, can be used as the above mentioned specific binding substance.

Here, in the "oligonucleotide" or in the "polynucleotide", deoxyribonucleic acid (DNA), ribonucleic acid (RNA) and peptide nucleic acid (PNA) are comprised. "PNA" refers to an artificially synthesized nucleic acid obtained by converting the phosphodiester bond of DNA into a peptide bond. The chain length of the oligonucleotide or polynucleotide bound to the aforementioned insoluble particles maybe selected appropriately, based on the object of the analysis, for example, it may be determined based on the chain length of a complementary sequence of DNA, RNA or PNA to be captured.

The synthesis of oligonucleotide used as the above mentioned specific binding substance can generally be carried out by using an automatic synthesizing device. Moreover, in can be carried out by a conventional genetic engineering technique such as PCR (polymerase chain reaction).

When the fluorescent probe of the present invention is applied to an immunological assay, an antigen (including hapten) or an antibody, which binds specifically to a substance to be analyzed or detected, can be used as the specific binding substance. In this case, the substance to be analyzed or detected is not particularly limited as long as the substance is a component generally contained in the sample to be tested and also a substance which can be immunologically detected. Examples of such a substance include proteins of various types, polysaccharides, lipid, biomass, various types of environmental substance and the like. More specific examples thereof include immunoglobulin (for example, IgG, IgM or IgA), infection disease-associated marker (for example, HBs antigen, HBs antibody, HIV-1 antibody, HIV-2 antibody, HTLV-1 antibody, or treponemal antibody), tumor-associated antigen (for example, AFP, CRP, or CEA), coagulation/fibrinogenolysis marker (for example, plasminogen, antithrombin-III, D-dimer, TAT, or PPI), antiepileptics (for example, hormone), various types of medical agents (for example, digoxin), biomass (for example, O-157, or Salmonella) or endotoxin or exotoxin thereof, microorganisms, enzymes, agricultural chemicals residue, and environmental endocrine disrupters. Either polychlonal antibody or monoclonal antibody, which can be obtained by the conventional method, can be used as the antibody used as the specific binding substance. Further, as the antibody, antibody which has been subjected to a protein (for example, enzyme such as pepsin or papain) treatment, for example, antibody fragments such as Fab, Fab', F(ab')$_2$, or Fv, may be used.

As described above, the fluorescent probe of the present invention can be used for detection or analysis of biopolymer of various types. Further, the fluorescent probe of the present invention has an advantage that, when excitation light is irradiated, no damage is done to biopolymer to be detected or analyzed.

The present invention is not limited to the aforementioned embodiment. The aforementioned embodiment is an example, and whatever is substantially equivalent in structure and has similar effect to the technological thoughts described in the claims of the present invention, is included to the technological scope of the present invention.

EXAMPLES

Hereinafter, the present invention will be described in detail with reference to the following examples.

1. Production of Core Portion, or the Second Fine Particles Containing a Rare Earth Element First, a method for producing a core portion containing a rare earth element characterized in emitting the up-conversion emission will be described.

1-1. $Y_2O_3$: Yb, Er Fine Particles $Y_2O_3$: Yb, Er fine particles were produced by preparing a precursor doped with Yb and Er, by a liquid phase reaction, and then by calcination of the precursor. The manufacturing process is as follows.

First, 0.0158 mol of yttrium nitrate, 0.004 mol of ytterbium nitrate and 0.0002 mol of erbium nitrate were dissolved in distilled water such that the volume of the mixture was 100 ml, thereby preparing a Y, Yb, Er ion-mixture solution. 100 ml of sodium carbonate aqueous solution (0.3 mol/l) was added to the above mentioned Y, Yb, Er ion-mixture solution, and the mixture was stirred for 2 hours.

Next, the mixture was subjected to centrifugation three times, each at 3000 rpm for 30 minutes, by using a centrifuge. Thereafter, the precipitation was dried in vacuum at 45° C. for hours, whereby basic yttrium carbonate doped with Yb and Er, as a precursor, was obtained.

The obtained precursor was put in an electric oven and rapidly heated, after being maintained in the oven at 900° C. for 30 minutes in the air atmosphere, the precursor was taken out of the oven and rapidly cooled. As a result, $Y_2O_3$: Yb, Er fine particles were synthesized. From the measurement results of SEM and XRD, it was confirmed that the average particle diameter was approximately 30 nm.

Figure 4:
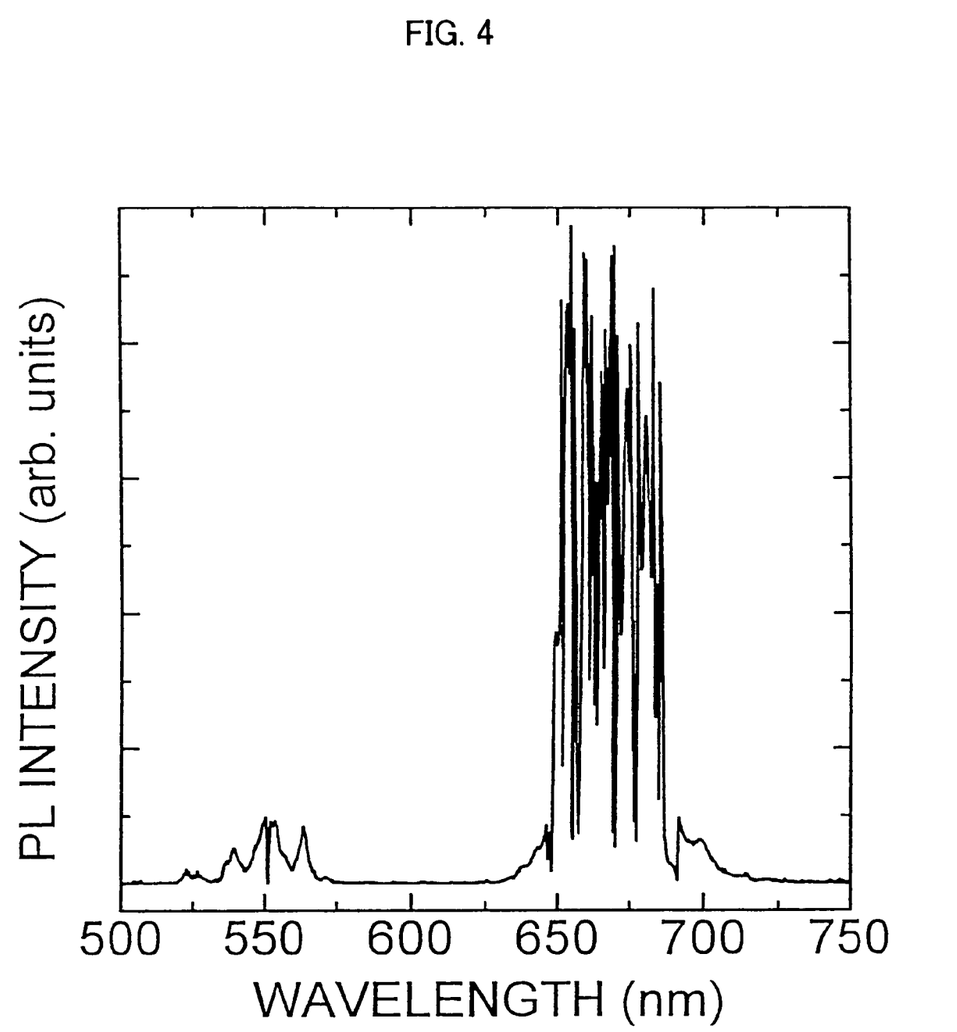
FIG. 4 is a graph showing light emitting spectrum resulting from excitation by semiconductor laser (980 nm) of $Y_2O_3$: Yb, Er fine particles.

The light emitting spectrum of the resulting $Y_2O_3$: Yb, Er fine particles of light excitation by a semiconductor laser (980 nm) is shown in FIG. 4. Emission of green color of $Er^{3+}$ is observed in the vicinity of 550 nm and emission of red color of Yb 3+is observed in a wavelength range of 650 to 680 nm.

It should be noted that FIG. 4 shows light emitting spectrum of $Y_2O_3$: Yb, Er fine particles to which erbium was added by the amount of 1 mol % and ytterbium was added by the amount of 20 mol %.

1-2. $Y_2O_3$: Er Fine Particles $Y_2O_3$: Er fine particles were produced by preparing a precursor doped with Er, by a liquid phase reaction, and then by calcination of the precursor. The manufacturing process is as follows.

First, 0.0198 mol of yttrium nitrate and 0.0002 mol of erbium nitrate were dissolved in distilled water such that the volume of the mixture was 100 ml, thereby preparing a Y, Er ion-mixture solution. 100 ml of sodium carbonate aqueous solution (0.3 mol/l) was added to the above mentioned Y, Er ion-mixture solution, and the mixture was stirred for 2 hours.

Next, the mixture was subjected to centrifugation three times, each at 3000 rpm for 30 minutes, by using a centrifuge. Thereafter, the precipitation was dried in vacuum at 45° C. for 5 hours, whereby basic yttrium carbonate doped with Er, as a precursor, was obtained.

The obtained precursor was put in an electric oven and rapidly heated, after being maintained at 900° C. for 30 minutes in the air atmosphere, the precursor was taken out of the oven and rapidly cooled. As a result, $Y_2O_3$: Er fine particles were synthesized. From the measurement results of SEM and XRD, it was confirmed that the average particle diameter was approximately 30 nm.

Figure 5:
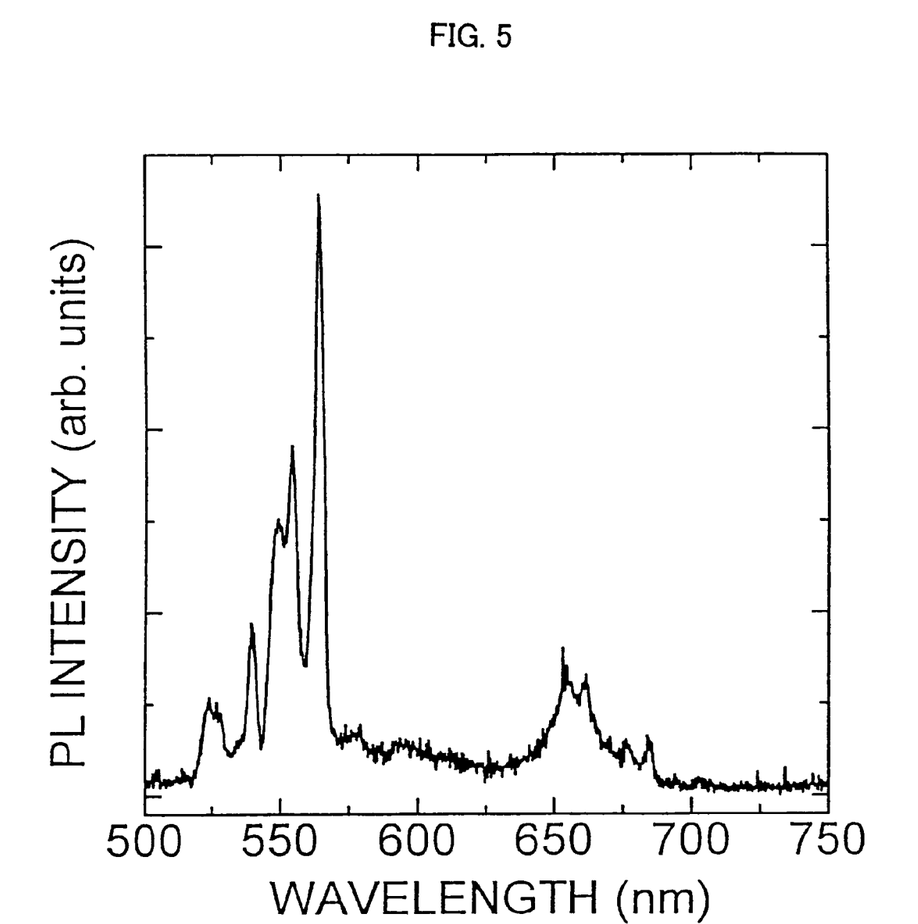
FIG. 5 is a graph showing light emitting spectrum resulting from excitation by semiconductor laser (980 nm) of $Y_2O_3$: Er fine particles.

The light emitting spectrum of the resulting $Y_2O_3$: Er fine particles of light excitation by a semiconductor laser (980 nm) is shown in FIG. 5. Emission of green color of $Er^{3+}$ is observed in the vicinity of 550 nm.

It should be noted that FIG. 5 shows light emitting spectrum of $Y_2O_3$: Er fine particles to which erbium was added by the amount of 1 mol %.

1-3. $Y_2O_3$: Yb, Tm Fine Particles $Y_2O_3$: Yb, Tm fine particles were produced by preparing a precursor doped with Yb and Tm, by a liquid phase reaction, and then by calcination of the precursor. The manufacturing process is as follows.

First, 0.0158 mol of yttrium nitrate, 0.004 mol of ytterbium nitrate and 0.0002 mol of thulium nitrate were dissolved in distilled water such that the volume of the mixture was 100 ml, thereby preparing a Y, Yb, Tm ion-mixture solution. 100 ml of sodium carbonate aqueous solution (0.3 mol/l) was added to the above mentioned Y, Yb, Tm ion-mixture solution, and the mixture was stirred for 2 hours.

Next, the mixture was subjected to centrifugation three times, each at 3000 rpm for 30 minutes, by using a centrifuge. Thereafter, the precipitation was dried in vacuum at 45° C. for 5 hours, whereby basic yttrium carbonate doped with Yb and Tm, as a precursor, was obtained.

The obtained precursor was put in an electric oven and rapidly heated, after being maintained at 900° C. for 30 minutes in the air atmosphere, the precursor was taken out of the oven and rapidly cooled. As a result, $Y_2O_3$: Yb, Tm fine particles were synthesized. From the measurement results of SEM and XRD, it was confirmed that the average particle diameter was approximately 30 nm.

Figure 6:
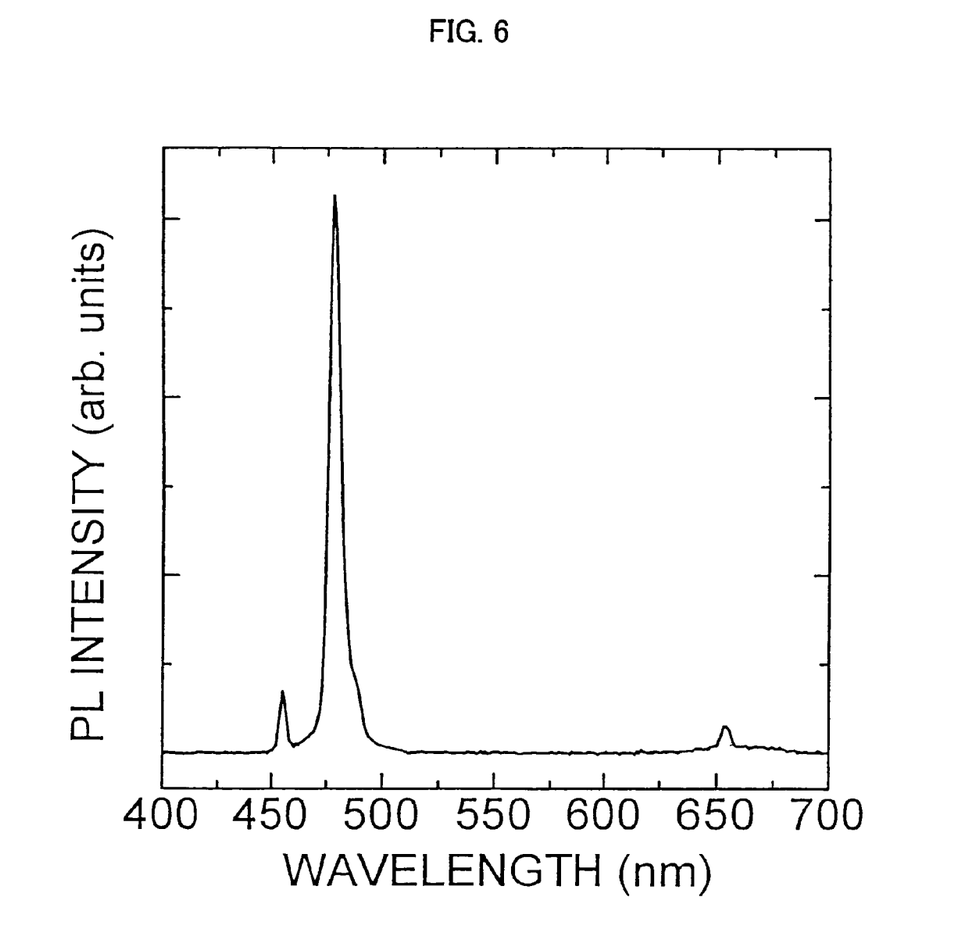
FIG. 6 is a graph showing light emitting spectrum resulting from excitation by semiconductor laser (980 nm) of $Y_2O_3$: Yb, Tm fine particles.

The light emitting spectrum of the resulting $Y_2O_3$: Yb, Tm fine particles of light excitation by a semiconductor laser (980 nm) is shown in FIG. 6. Emission of blue color of $Tm^{3+}$ is observed in the vicinity of 480 nm.

It should be noted that FIG. 6 shows light emitting spectrum of $Y_2O_3$: Yb, Tm fine particles to which thulium was added by the amount of 1 mol % and ytterbium was added by the amount of 20 mol %.

2. Production of the First Fine Particles Containing a Rare Earth Element 2-1. $Y_2O_3$: Yb, Er/APTS Fine Particles 300 mg of $Y_2O_3$: Yb, Er fine particles synthesized in the aforementioned 1.1 was first dispersed in a small amount of dry toluene containing 30 mg of a polymer dispersion stabilizer and then the mixture was diluted with additional dry toluene such that the total weight of the mixture was 10 g. 0.5 g of (3-aminopropyl)trimethoxysilane (APTS) was added to the thus obtained fine-particle-dispersed solution in nitrogen atmosphere, with vigorous stirring. The stirring was continued at the room temperature for 15 hours.

Then, the APTS-treated fine particles were collected by using a centrifuge. Thereafter, the collected fine particles were dispersed to toluene again, centrifuged, collected, dispersed to toluene:methanol (1:1), centrifuged, collected, dispersed to methanol, centrifuged, collected, dispersed to methanol:water (1:1), centrifuged, collected, finally dispersed to water and centrifuged, whereby $Y_2O_3$: Yb, Er/APTS composite fine particles were obtained.

The yield was 210 mg. The dried composite fine particles were successfully dispersed to water again. This composite fine particle exhibited up-conversion emission, both in a dry state and in a water-dispersed state, having spectrum shape similar to that of FIG. 4.

2-2. $Y_2O_3$: Er/PEG-Biotin Fine Particles

By using 300 mg of the $Y_2O_3$: Er fine particles synthesized in the aforementioned 1-2, $Y_2O_3$: Er/APTS composite fine particles were produced in a manner similar to that of 2-1. The yield was 233 mg. 200 mg of $Y_2O_3$: Er/APTS composite fine particles were dispersed again to 5 g of water of pH 8.

A solution, prepared by adding 30 mg of Biotin-PEG-NHS (compound 16 shown above, manufactured by Shearwater Co. Ltd., catalogue No. OH2ZOF02) to 5 g of water of pH 8, was added to the above dispersion liquid. The mixture was stirred for 1 hour. Thereafter, the Biotin-PEG-NHS treated composite fine particles was separated from the supernatant liquid by centrifuge, the composite fine particles were dispersed to water again, centrifuged and collected repeated for three times. Thereafter, the composite fine particles were purified by dialysis, whereby the target $Y_2O_3$: Er/PEG-Biotin composite fine particles were obtained.

The total weight of the obtained dispersion solution of $Y_2O_3$: Er/PEG-Biotin composite fine particles was 33.4 g. The yield of $Y_2O_3$: Er/PEG-Biotin composite fine particles, which was obtained by collecting a portion thereof and measuring a change in weight of before and after being dried, was 74 mg. The composite particles exhibited up-conversion emission, both in a dry state and in a water-dispersed state, having spectrum shape similar to that of FIG. 5.

2-3. $Y_2O_3$: Er/(APTS-containing Layer) Fine Particles 20 mmol of anhydrous yttrium acetate and 0.4 mmol of anhydrous erbium acetate were dispersed to anhydrous ethanol. The obtained anhydrous ethanol dispersion solution was refluxed for 3 hours and then cooled to the room temperature. While being cooled to 0° C. and with vigorous stirring being irradiated with ultrasonic wave, an anhydrous methanol solution of tetramethylammonium hydroxide was added thereto, whereby $Y_2O_3$: Er fine particles were produced. The amount of added tetramethylammonium was approximately 22 mmol.

To this $Y_2O_3$: Er fine particles dispersion solutuin, an anhydrous toluene solution containing 0.01 mmol of tetraethoxysilane and 0.01 mmol of APTS was added. The mixture was allowed to be reacted in nitrogen atmosphere for further 2 hours, whereby $Y_2O_3$: Er/(APTS-containing layer) composite fine particles were produced. The dispersion liquid of $Y_2O_3$: Er/(APTS-containing layer) composite fine particles, which agglutinate was removed, was twice subjected to the process in which the fine particles were collected by centrifugation and dispersed to ethanol. The obtained fine particles dispersion liquid was flowed into a dialysis tube with a stirrer bar, and stirred with a magnetic stirrer, in water of pH 3.8, for 3 days, with water constantly being replaced. Thereafter, semiconductor laser (980 nm) was irradiated to the resulting to-water dispersion liquid of $Y_2O_3$: Er/(APTS-containing layer) composite fine particles in a dark place. It was confirmed that the irradiated portion emitted green color light. The average particle diameter measured by a transmission electron microscope was approximately 11 nm.

2-4. $LaF_3$: Yb, Er/(APTS-containing Layer) Fine Particles 120 mmol of di-n-octadecyldithiophosphate (DOSP) and 120 mmol of sodium fluoride were added to 4 L of an ethanol/water mixed solvent (10:1), and heated to 75° C. To this heated mixture solution, 100 ml of an aqueous solution containing 40 mmol of lanthanum nitrate, 0.12 mmol of ytterbium nitrate and 0.01 mmol of erbium nitrate was added dropwise and was continued to be heated at 75° C. for 2 hours. After the mixture solution was cooled to the room temperature, rough $LaF_3$: Yb, Er/(DOSP-containing layer) fine particles were separated by centrifugation and the cleaned with water and ethanol for five times each. Thereafter, the fine particles were dispersed to dichloromethane, precipitated again by adding ethanol. The precipitation was separated by centrifugation. This process was repeated for three times, whereby $LaF_3$: Yb, Er/(DOSP-containing layer) fine particles were purified. The solid content obtained after being vacuum-dried at the room temperature for 24 hours weighed 6.9 g. The obtained $LaF_3$: Yb, Er/(DOSP-containing layer) fine particles were dispersible to dichloromethane or toluene, but not dispersible to ethanol and water. 5 g of $LaF_3$: Yb, Er/(DOSP-containing layer) fine particles was dispersed to 500 ml of anhydrous toluene in nitrogen atmosphere. To this, 10 ml of anhydrous toluene in which 0.02 mmol of tetraethoxysilane and 0.02 mmol of APTS had been dissolved was added, and the mixture was allowed to be reacted for 15 hours. After being collected by centrifugation, dispersion to ethanol was attempted. After 5 hours of still standing, the supernatant liquid was separated by decantation. The separated supernatant liquid was centrifuged and the solid content was dispersed to ethanol/water (1:1). Centrifugation and dispersion to water of pH 3.5 were attempted. As agglutinate was hardly observed at this stage, it was confirmed that $LaF_3$: Yb, Er/(APTS-containing layer) fine particles had been produced. The above was collected by centrifugation and vacuum-dried at the room temperature for 24 hours. The weight after being dried was 4.1 g. When semiconductor laser beam of 980 nm was irradiated thereon, it emitted light of red color. From the SEM observation, it was confirmed that the average particle diameter was approximately 32 nm.

The invention claimed is:

1. A fine particle containing a rare earth element, which is excited by light having a wavelength in a range of 500 nm to 2000 nm and thereby emits up-conversion emission, wherein the fine particle containing a rare earth element comprises:
a core portion containing the rare earth element; and
a functional shell portion modifying a surface of the core portion;
wherein the functional shell portion comprising at least a specific binding substance binding site which can be bound to a specific binding substance, and
wherein the functional shell portion further comprises an agglutinate preventing site which prevents agglutination of the fine particles containing a rare earth element, and
wherein the agglutinate preventing site is at least one functional group selected from the group consisting of ethylene oxide site, phosphate ester site, betaine site, sulphonic group and imino group.

2. The fine particle containing a rare earth element according to claim 1, wherein the specific binding substance binding site is at least one of, a site with condensation reactivity, a site with addition reactivity, a site with substitution reactivity, or a site capable of effecting a specific interaction.

3. The fine particle containing a rare earth element according to claim 1, wherein the agglutinate preventing site is at least one of a site having hydrogen bonding, or a site with hydrating ability.

4. The fine particle containing a rare earth element according to claim 1, wherein the functional shell portion comprises a core portion binding site, which binds to the core portion.

5. The fine particle containing a rare earth element according to claim 4, wherein the core portion binding site is at least one of, a site with a function to bind to a metal, a site with condensation reactivity, a site with addition reactivity, or a site with substitution reactivity.

6. The fine particle containing a rare earth element according to claim 1, wherein the average particle diameter of the core portion is in a range of 1 to 100 nm.

7. The fine particle containing a rare earth element according to claim 1, wherein the core portion is made of a halide or an oxide as a parent material, and comprises a rare earth element which can emit the up-conversion emission.

8. The fine particle containing a rare earth element according to claim 1, wherein the rare earth element is at least one of rare earth element selected from the group consisting of erbium (Er), holmium (Ho), praseodymium (Pr), thulium (Tm), neodymium (Nd), gadolinium (Gd), europium (Eu), ytterbium (Yb), samarium (Sm) and cerium (Ce).

9. The fine particle containing a rare earth element according to claim 1, wherein the fine particle containing a rare earth element is a fine particle of 1 to 100 nm average particle diameter of an oxide doped with the rare earth element, and the oxide is at least one kind selected from the group consisting of yttrium oxide, gadolinium oxide, lutetium oxide, lanthanum oxide and scandium oxide.

10. The fine particle containing a rare earth element according to claim 9, wherein the rare earth element is erbium and ytterbium.

11. The fine particle containing a rare earth element according to claim 9, wherein the rare earth element is erbium.

12. The fine particle containing a rare earth element according to claim 9, wherein the rare earth element is thulium and ytterbium.

13. A fluorescent probe comprising; the fine particle containing a rare earth element according to claim 1; and a specific binding substance which binds to the fine particle containing a rare earth element.

14. A fluorescence probe according to claim 13, wherein the specific binding substance is any one of, polynucleotide, hormone, protein, antigen, antibody, peptide, cell or tissue.

* * * * *